United States Patent [19]

Fujioka et al.

[11] Patent Number: 4,540,812

[45] Date of Patent: * Sep. 10, 1985

[54] 2-ACETOXY-4-(2-BORNYLOXY) BUTANE

[75] Inventors: Futoshi Fujioka, Wanamassa; Richard M. Boden, Ocean; William L. Schreiber, Jackson, all of N.J.

[73] Assignee: International Flavors & Fragrances Inc., New York, N.Y.

[*] Notice: The portion of the term of this patent subsequent to Jun. 4, 2002 has been disclaimed.

[21] Appl. No.: 578,346

[22] Filed: Feb. 9, 1984

Related U.S. Application Data

[63] Continuation-in-part of Ser. No. 574,150, Jan. 26, 1984, which is a continuation-in-part of Ser. No. 533,915, Sep. 19, 1983, which is a continuation-in-part of Ser. No. 507,292, Aug. 1, 1983, abandoned.

[51] Int. Cl.³ .............................................. C07C 69/14
[52] U.S. Cl. ................................ 560/256; 252/522 R; 252/522 A; 252/174.11; 424/69
[58] Field of Search ........................................ 560/256

[56] References Cited

U.S. PATENT DOCUMENTS 4,439,354  3/1984  Light et al. ................... 560/256 X
4,448,984  5/1984  Specker et al. ................... 560/256

Primary Examiner—Bernard Helfin
Attorney, Agent, or Firm—Arthur L. Liberman

[57] ABSTRACT

Described is the 2-acetoxy-4-(2-bornyloxy) butane of our invention defined according to the structure:

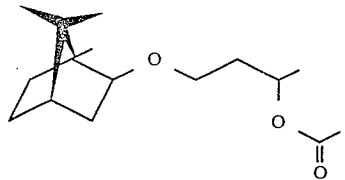

as well as methods for augmenting or enhancing the aroma of consumable materials including perfumes, colognes and perfumed articles by adding thereto an aroma augmenting or enhancing quantity of the 2-acetoxy-4-(2-bornyloxy) butane of our invention.

1 Claim, 7 Drawing Figures

FIG.1

GLC PROFILE FOR EXAMPLE I.
CRUDE

FIG.3

GLC PROFILE FOR EXAMPLE II.
CRUDE

FIG. 2 NMR SPECTRUM FOR FRACTION 2 OF EXAMPLE I

FIG. 4

GLC PROFILE FOR FRACTION 9 OF EXAMPLE II.

FIG. 5

NMR SPECTRUM FOR FRACTION I OF EXAMPLE II.

2-ACETOXY-4-(2-BORNYLOXY) BUTANE

This application is a continuation-in-part of application for U.S. Letters Patent, Ser. No. 574,150 filed on Jan. 26, 1984, which in turn, in a continuation-in-part of application for U.S. Letters Patent, Ser. No. 533,915 filed on Sept. 19, 1983, which in turn, is a continuation-in-part of application for U.S. Letters Patent, Ser. No. 507,292 filed on Aug. 1, 1983 and now abandoned.

BACKGROUND OF THE INVENTION

The instant invention provides the 2-acetoxy-4-(2-bornyloxy) butane of our invention defined according to the structure:

as well as the use thereof for augmenting or enhancing the aroma of perfume compositions, colognes and perfumed articles.

Inexpensive chemical compositions of matter which can provide woody, patchouli and sandalwood aromas with woody, patchouli and velvety topnotes are highly desirable in the art of perfumery. Many of the natural materials which provide such fragrances and contribute desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

Oxo reaction products have heretofore been produced for augmenting or enhancing the aroma of perfume compositions, perfumed articles and colognes. Thus, ether carboxaldehydes are well known in the art of perfumery for augmenting or enhancing the aroma of perfume compositions or perfumed articles. U.S. Pat. No. 4,359,390 issued on Nov. 16, 1982, the specification for which is incorporated by reference herein, discloses the use of such ether carboxaldehydes such as the compound having the structure:

in augmenting or enhancing the aroma of perfume compositions, colognes and perfumed articles. Application for U.S. Letters Patent, Ser. No. 335,794 filed on Sept. 26, 1983, the specification for which is incorporated by reference herein, discloses 5-alkoxy-bicyclo[2.2.1]heptane-2-oxypropane derivatives. The invention of Ser. No. 335,794 relates to 5-alkoxy-bicyclo[2.2.1]heptane-2-oxypropane derivatives defined according to the structure:

(wherein R represents $C_1$–$C_3$ alkyl and wherein Z represents one of the moieties, carbinol having the structure:

or carboxaldehyde having the structure:

and uses thereof in augmenting or enhancing the aroma of perfume compositions, colognes or perfumed articles (e.g., solid or liquid anionic, cationic, nonionic or zwitterionic detergents, fabric softener compositions, fabric softener articles, cosmetic powders, hair preparations, perfumed polymers and the like).

Nothing in the prior art, however, suggests the 2-acetoxy-4-(2-boronyloxy) butane of our invention or organoleptic uses of same.

BRIEF DESCRIPTION OF THE DRAWINGS

(Conditions: Field strength: 100 MHz; solvent: $CFCl_3$).

(Conditions: SE-30 column programmed at 100°–220° C. at 8° per minute).

(Conditions: Field strength: 100 MHz; solvent: $CFCl_3$).

DETAILED DESCRIPTION OF THE DRAWINGS

Figure 3:
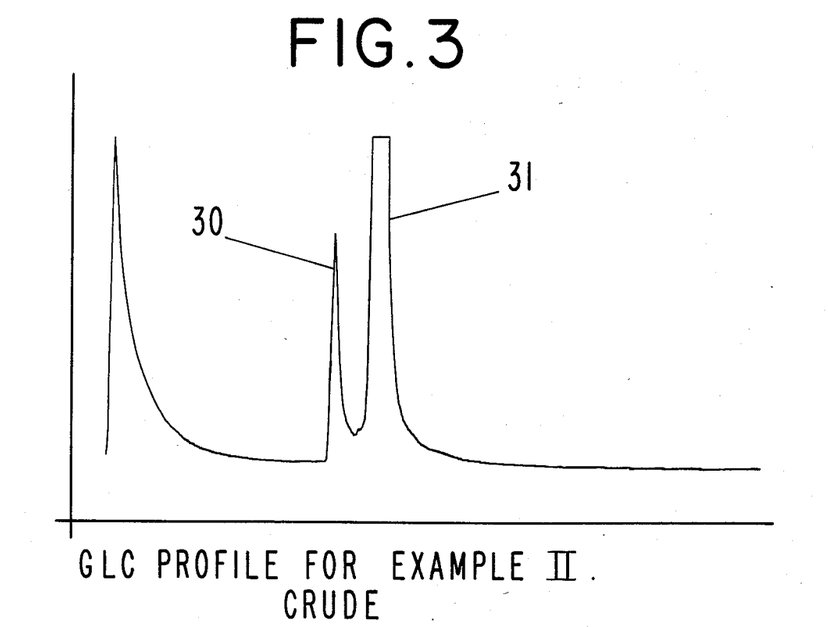
FIG. 3 is the GLC profile for the crude reaction product of Example II containing the compound having the structure.
Figure 6:
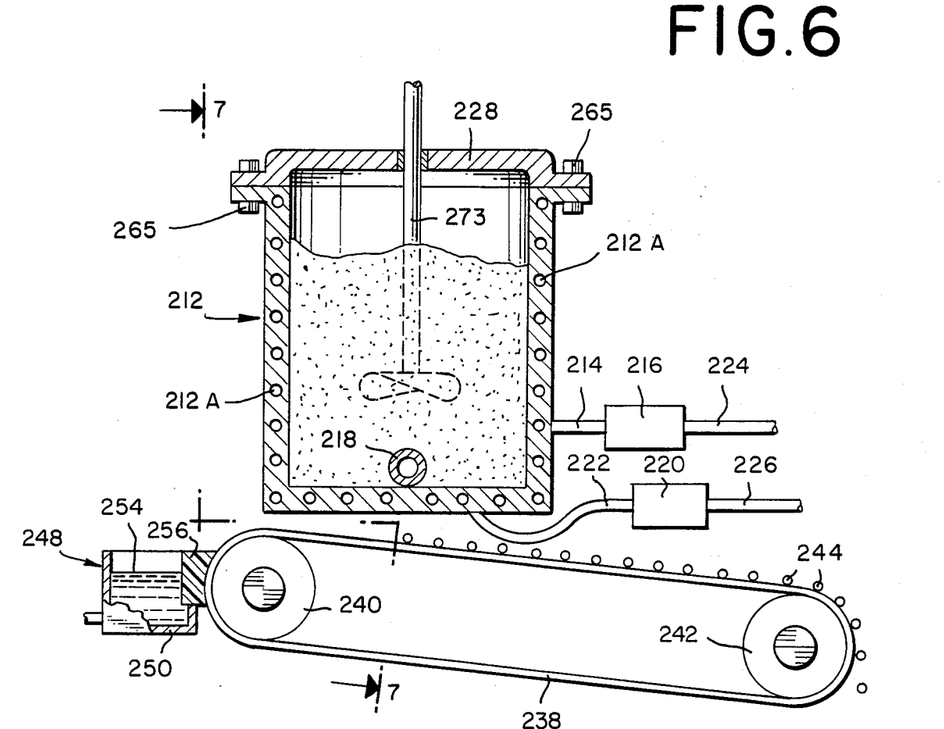
FIG. 6 represents a cutaway side elevation view of the apparatus used in forming perfumed polymers which contain embedded therein the 2-acetoxy-4-(2-bornyloxy) butane of our invention.
Figure 7:
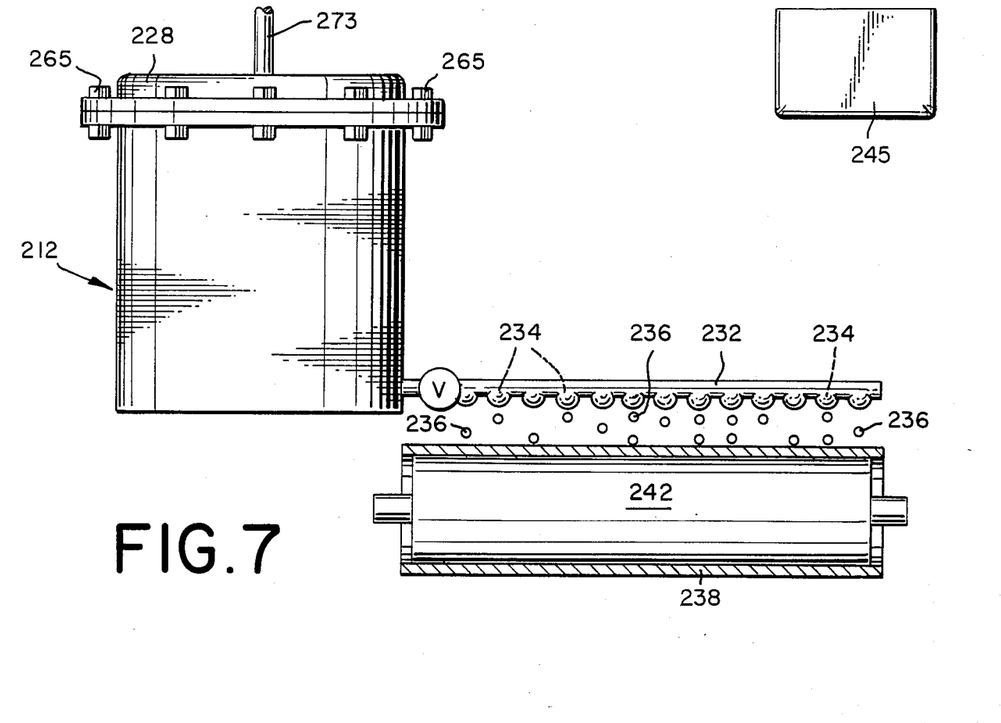
FIG. 7 is a front view of the apparatus of FIG. 6 looking in the direction of the arrows.

FIG. 3 is the GLC profile for the crude reaction product of Example II containing the compound having the structure:

as well as the starting material having the structure:

The peak indicated by Reference 30 is the peak for the starting material having the structure:

The peak indicated by Reference 31 is the peak for the reaction product having the structure:

Referring to FIGS. 6 and 7, there is provided a process for forming scented polymer elements (wherein the polymer may be a thermoplastic polymer such as a low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 6 and 7, in particular, the apparatus used in producing such elements comprises a device for forming the polymer containing perfume, e.g., polyethylene or polyethylene-polyvinyl acetate or mixtures of same or polypropylene containing the 2-acetoxy-4-(2-bornyloxy) butane of our invention taken alone or taken together with one or more additional perfume materials, which comprises a vat or container 212 into which the polymer taken alone or in admixture with other copolymers and the perfuming substance which is at least the 2-acetoxy-4-(2-bornyloxy) butane of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cyclinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 Sayboldt seconds.

The heater 218 is maintained to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains the 2-acetoxy-4-(2-bornyloxy) butane of our invention and, if desired, one or more of the perfume materials is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer is in intimate admixture with the 2-acetoxy-4-(2-bornyloxy)butane of our invention taken alone or taken further together with one or more other perfume substances and in such admixture will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature throught the controls 216 and 220 is essential in order to insure temperature balance to provide for the continuous dripping or dropping of molten polymer intimately admixed with the perfume substance which is all of or which contains the 2-acetoxy-4-(2-bornyloxy)butane of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides the 2-acetoxy-4-(2-bornyloxy)butane having the structure:

The present invention also provides a process for preparing the 2-acetoxy-4-(2-bornyloxy)butane by reacting the compound having the structure:

with an acylating agent such as acetic anhydride according to the reaction:

The present invention also provides a process for augmenting or enhancing the aroma of perfume compositions, colognes or perfumed articles by adding to such perfume composition, cologne or perfumed article the 2-acetoxy-4-(2-bornyloxy)butane of our invention having the structure:

The perfumed articles of our invention include soaps, anionic, cationic, nonionic or zwitterionic detergents, fabric softener compositions, fabric softener articles, optical brightener compositions, perfumed polymers, hair preparations and the like. Accordingly, a need in the field of perfumery, as well as in the field of perfumed articles and cosmetics manufacture, is fulfilled by augmenting or enhancing the specific aromas in such perfume compositions, colognes and perfume articles, e.g., woody, patchouli and sandalwood aromas with woody, patchouli and velvety topnotes.

The 2-acetoxy-4-(2-bornyloxy)butane of our invention defined according to the structure:

is prepared by reacting the compound having the structure:

with acetic anhydride or acetyl chloride or acetyl bromide.

The starting material having the structure:

is formed by means of reacting 1,3-butanediol with camphene according to Example VI of the parent case application for U.S. Letters Patent Ser. No. 574,150 filed on Jan. 26, 1984, the specification for which is incorporated by reference herein, according to the reaction:

The reaction of the compound having the structure:

with acetic anhydride according to the step:

takes place at a temperature in the range of from about 70° C. up to about 120° C. It is preferable when using acetyl chloride to carry out the reaction at the lower part of this temperature range and when using acetic anhydride to carry out the reaction at the upper part of the temperature range. The mole ratio of acylating agent:compound having the structure:

is about 1:1 with a slight excess of acylating agent to compound having the structure:

The reaction time may vary from about one hour up to about five hours depending upon the yield of reaction product desired. At the end the reaction, the reaction mass is washed with water, extracted with an inert solvent, such as toluene, and distilled, preferably, by means of fractional distillation to yield the compound having the structure:

The 2-acetoxy-4-(2-bornyloxy)butane prepared in accordance with the process of our invention and one or more auxiliary perfume ingredients including, for example, alcohols, ketones, aldehydes, terpinic hydrocarbons, nitriles, esters other than the 2-acetoxy-4-(2-bornyloxy)butane of our invention, lactones, natural essential oils and synthetic essential oils may be admixed so that the combined odors of the individual components produce a pleasant and desired fragrance, particularly and preferably in the woody, patchouli and sandalwood fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, the 2-acetoxy-4-(2-bornyloxy)butane of our invention prepared in accordance with the process of our invention can be used to alter, modify or enhance the aroma characteristics of a perfume composition, for example, by utilizing or moderating the olfactory reaction contributed by another ingredient in the composition.

The amount of the 2-acetoxy-4-(2-bornyloxy)butane of our invention prepared in accordance with the process of our invention, which will be effective in perfume compositions as well as perfumed articles (e.g., anionic, cationic, nonionic or zwitterionic solid or liquid detergents, soaps, fabric softener compositions, drier-added fabric softener articles, optical brightener compositions, perfumed polymers, textile sizing agents and the like) and colognes depends on many factors, including the other ingredients, their amounts and the effects which are desired. It has been found that perfume compositions containing as little as 0.01% of the 2-acetoxy-4-(2-bornyloxy)butane of our invention or even less (e.g., 0.005%) can be used to impart, augment or enhance woody, pathcouli and sandalwood aromas with woody, patchouli and velvety topnotes in or to soaps, cosmetics, solid or liquid anionic, nonionic, cationic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

The 2-acetoxy-4-(2-bornyloxy)butane of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and perfumed polymers and articles of manufacture produced from said perfumed polymers, e.g., garbage bags, children's toys and the like. When used as an olfactory component in perfumed articles, as little as 0.2% of the 2-acetoxy-4-(2-bornyloxy)butane of our invention prepared in accordance with the process of our invention will suffice to impart, augment or enhance woody, patchouli and sandalwood aromas with woody, patchouli and velvety topnotes. Generally, no more than 6% of the 2-acetoxy-4-(2-bornyloxy)butane of our invention based on the ultimate end product is required in the perfumed article. Accordingly, the range of 2-acetoxy-4-(2-bornyloxy)butane in the perfurmed article is from about 0.2% by weight of 2-acetoxy-4-(2-bornyloxy)butane up to about 6% by weight of the 2-acetoxy-4-(2-bornyloxy)butane based on the total weight of the perfumed article.

In addition, the perfume composition or fragrance composition of our invention can contain a vehicle or carrier for the 2-acetoxy-4-(2-bornyloxy)butane. The vehicle can be a liquid such as a non-toxic alcohol, e.g., ethyl alcohol, a non-toxic glycol, e.g., propylene glycol or the like. The carrier can also be an absorbent solid, such as a gum (e.g., gum arabic, guar gum, xanthan gum) or components for encapsulating the composition (such as, for example, gelatin as by coacervation or such as a urea formaldehyde prepolymer) which on polymerization forms a capsule shell around a liquid perfume scenter.

Our invention also relates to the utilization of controlled release technology for the controlled release of perfumes into gaseous environments from polymers such as mixtures of epsilon polycaprolactone polymers and polyethylene which polyepsilon caprolactone polymers are defined according to at least one of the structures:

wherein "n" is from about 50 up to about 1,200 with the proviso that the average "n" in the system varies from about 150 up to about 700 according to the mathematical statement:

$$[700 \geq \bar{\eta} \geq 150]$$

with the term $$\bar{\eta}$$

being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$(dM_t)/(dt) = k_1 e^{-k_2 t}$$

wherein $k_1$ and $k_2$ are constants. According to Kydonieus, "Controlled Release Technologies: Methods, Theory, and Applications" (cited, supra) the amount of perfume composition released is proportional to time as long as the concentration of perfume material present, e.g., the 2-acetoxy-4-(2-bornyloxy)butane of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the 2-acetoxy-4-(2-bornyloxy)butane of our invention.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMOPLASTIC POLYMERS PCL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilized the polyepsilon caprolactone useful in conjunction with our invention against discoloration are dihydroxybenzenes such hydroquinone or compounds having the formula:

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or absorbed into the polymeric matrix.

The method of incorporating the 2-acetoxy-4-(2-bornyloxy)butane of our invention or perfume compositions containing same into the polymers may be according to the techniques of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylenepolyepsilon caprolactone polymer mixture (50:50) is mixed with the 2-acetoxy-4-(2-bornyloxy)butane of our invention. Drops are formed from the mixture and the drops are then melted, if desired, with a second amount of unscented low density polyethylene, for example, or polypropylene, for example. Usually, but not necessarily, the second amount of polymer is larger than the first amount. The resulting mixture thus obtained, is solidified subsequent to or prior to ultimate casting into a utilitarian shape.

Thus, in accordance with one aspect of our invention, the imparting of scent is effected in two stages. In a first stage, a 50:50 (weight:weight) polyepsilon caprolactone, e.g., PCL-700: polyethylene in molten form is admixed with a high percentage of the 2-acetoxy-4-(2-bornyloxy)butane of our invention and the mixture is solidified in the form of pellets or beads. These pellets or beads thus contain a high percentage of the 2-acetoxy-4-(2-bornyloxy)butane (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention the 2-acetoxy-4-(2-bornyloxy)butane of our invention is added to the polymer in a large closed container or drum which is maintained under controlled temperature conditions while the polymer in a melted condition is mixed with the 2-acetoxy-4-(2-bornyloxy)butane under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by the 2-acetoxy-4-(2-bornyloxy)butane of our invention is permitted to drip through the orifices onto a continuously moving, cooled conveyor upon which the polymer containing the 2-acetoxy-4-(2-bornyloxy)butane of our invention solidifies into small size pellets with the perfume imprisoned therein. The apparatus useful in conjunction with this process, advantageously includes a conveyor of a material which will not adhere to the polymer which contains the 2-acetoxy-4-(2-bornyloxy)butane of our invention.

In order that the droplets form into uniform pellets or beads, the conveyor is continuously washed with a liquid, such as water to maintain the surface relatively cool. The pellets are delivered by the conveyor into a container and packaged for shipment.

The following Example I illustrates a process for preparing the precursor having the structure:

for making the product having the structure:

of our invention. The following Example II illustrates a process for preparing the 2-acetoxy-4-(2-bornyloxy)butane of our invention. The examples following Example II are illustrative of the organoleptic utilities of the 2-acetoxy-4-(2-bornyloxy)butane of our invention. All parts and percentages given herein are by weight unless otherwise specified.

EXAMPLE I

Preparation of 4-(2-bornyloxy)2-butanol

Reaction:

Into a one liter reaction vessel equipped with stirrer, thermometer, reflux condenser and heating mantle is placed 340 grams of 1,3-butanediol and 10 grams of boron trifluoride. The reaction mass is heated to 80° C. and while maintaining the reaction mass at 80° C., 340 grams of camphene is added over a two hour period. At the end of the camphene feeding period, the reaction mass is stirred at a temperature of 80° C. for a period of 18 hours.

After the 18 hour period, the reaction mass is quenched with water and the reaction mass is washed with saturated sodium carbonate solution until neutral. The aqueous phase is separated from the organic phase. The aqueous phase is extracted with toluene and the toluene extracts are added to the organic phase. The resulting organic material is then charged to an evaporator and the toluene solvent is recovered.

The resulting product is distilled on a splash column packed with saddles yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 93/ | 127/ | 5.0 | 7.0 |
| 2 | 115 | 127 | 5.0 | 15.0 |
| 3 | 123 | 136 | 4.8 | 211.0 |
| 4 | 175 | 220 | 3.8 | 190.0 |

Figure 1:
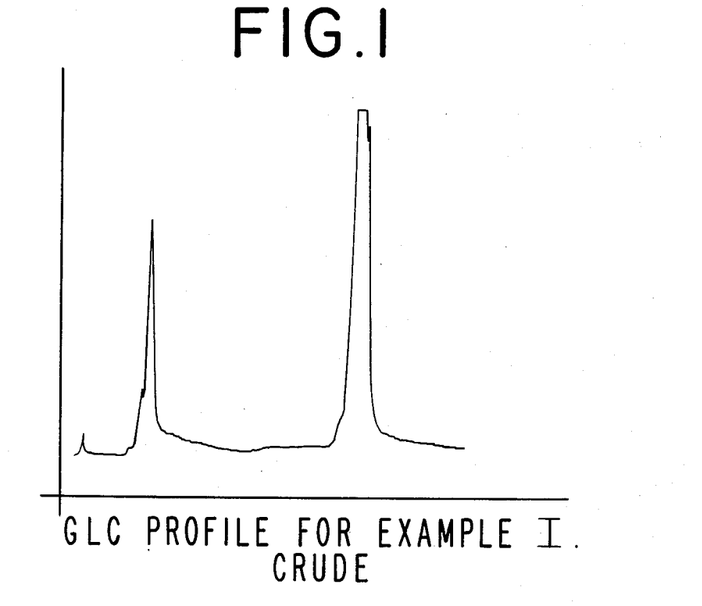
FIG. 1 is the GLC profile for the crude reaction product of Example I containing the compound having the structure.
Figure 2:
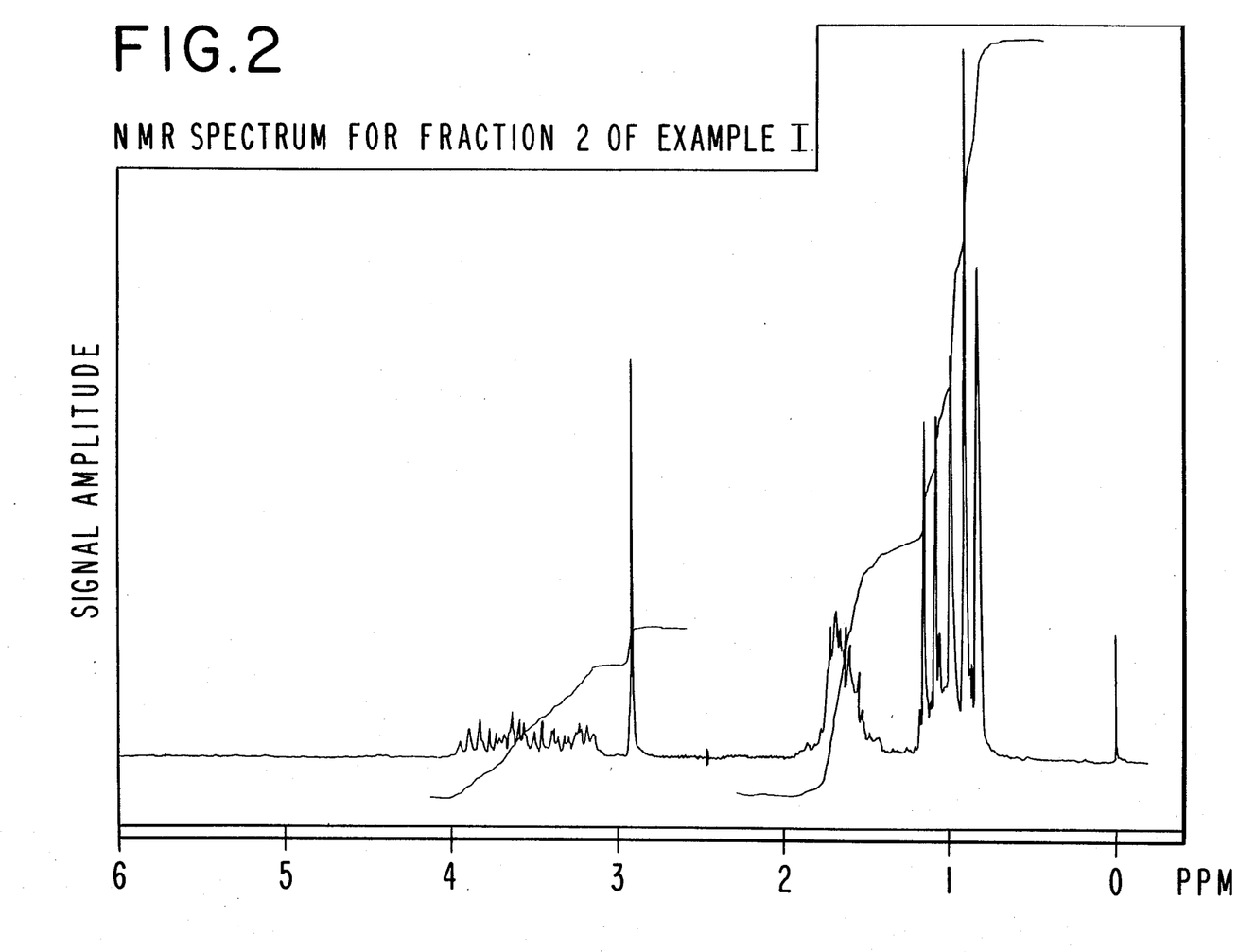
FIG. 2 is the NMR spectrum for fraction 2 of the distillation product of the reaction product of Example I containing the compound having the structure.

FIG. 1 is the GLC profile for the crude reaction product containing the compound having the structure:

FIG. 2 is the NMR spectrum for fraction 2 of the foregoing distillation product containing the compound having the structure:

(Conditions: Field strength: 100 MHz; solvent: $CFCl_3$).

EXAMPLE II

Preparation of 2-acetoxy-4-(2-bornyloxy)butane

Reaction:

Into a 1000 cc flask equipped with stirrer, theromoter, reflux condenser and heating mantle is placed 168 grams of acetic anhydride (1.65 moles). The acetic anhydride is heated to 100° C. Over a period of one hour, while maintaining the temperature at 95°–100° C., the compound having the structure:

prepared according to Example I is added to the reaction mass. At the completion of the feeding of the compound having the structure:

the reaction mass is stirred at 98° C. for a period of three hours. At the end of the three hour period, the reaction mass is washed with water and extracted with toluene. The toluene extract is evaporated and the toluene is recovered. The resulting product is distilled on a 12" Goodloe column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 103/105 | 133/141 | 1.2 | 5.0 |
| 2 | 116 | 158 | 1.1 | 0 |
| 3 | 116 | 154 | 1.1 | 19.0 |
| 4 | 116 | 154 | 1.1 | 28.0 |
| 5 | 116 | 154 | 1.1 | 29.0 |
| 6 | 116 | 154 | 1.1 | 32.0 |
| 7 | 116 | 154 | 1.1 | 31.0 |
| 8 | 116 | 154 | 1.1 | 20.0 |
| 9 | 128/134 | 151/152 | 1.6/1.6 | 9.0 |
| 10 | 122 | 154 | 1.6 | 6.0 |
| 11 | 128 | 162 | 2.2 | 14.0 |
| 12 | 118 | 164 | 1.2 | 11.0 |
| 13 | 120 | 164 | 1.3 | 10.0 |
| 14 | 123 | 167 | 1.6 | 14.0 |
| 15 | 121 | 176 | 1.3 | 22.0 |
| 16 | 121 | 176 | 1.3 | 14.0 |
| 17 | 123 | 183 | 1.6 | 14.0 |
| 18 | 120 | 196 | 1.3 | 12.0 |
| 19 | 120 | 216 | 1.3 | 8.0 |

Fractions 3-17 are bulked. The bulked fractions have a woody, patchouli and sandalwood aroma with woody, patchouli and velvety topnotes.

Figure 4:
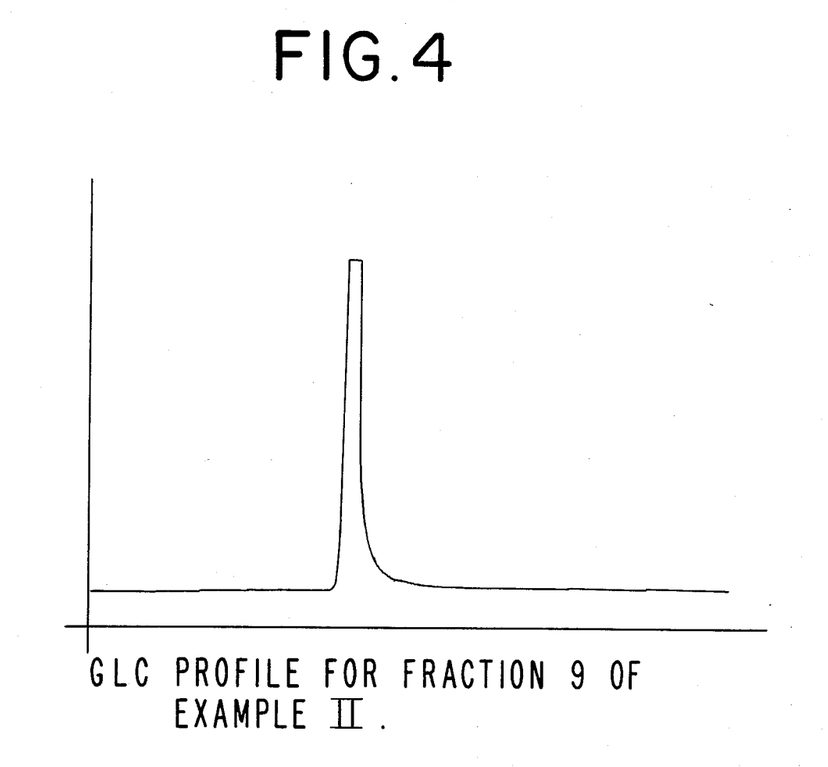
FIG. 4 is the GLC profile for fraction 9 of the distillation product of the reaction product of Example II containing the compound having the structure.

FIG. 3 is the GLC profile for the crude reaction product. The peak indicated by reference 30 is the peak for the starting material containing the compound having the structure:

The peak indicated by reference 31 is the peak for the compound having the structure:

FIG. 4 is the GLC profile for fraction 9 of the foregoing distillation (Conditions: SE-30 column programed at 100°-220° C. at 8° C. per minute).

Figure 5:
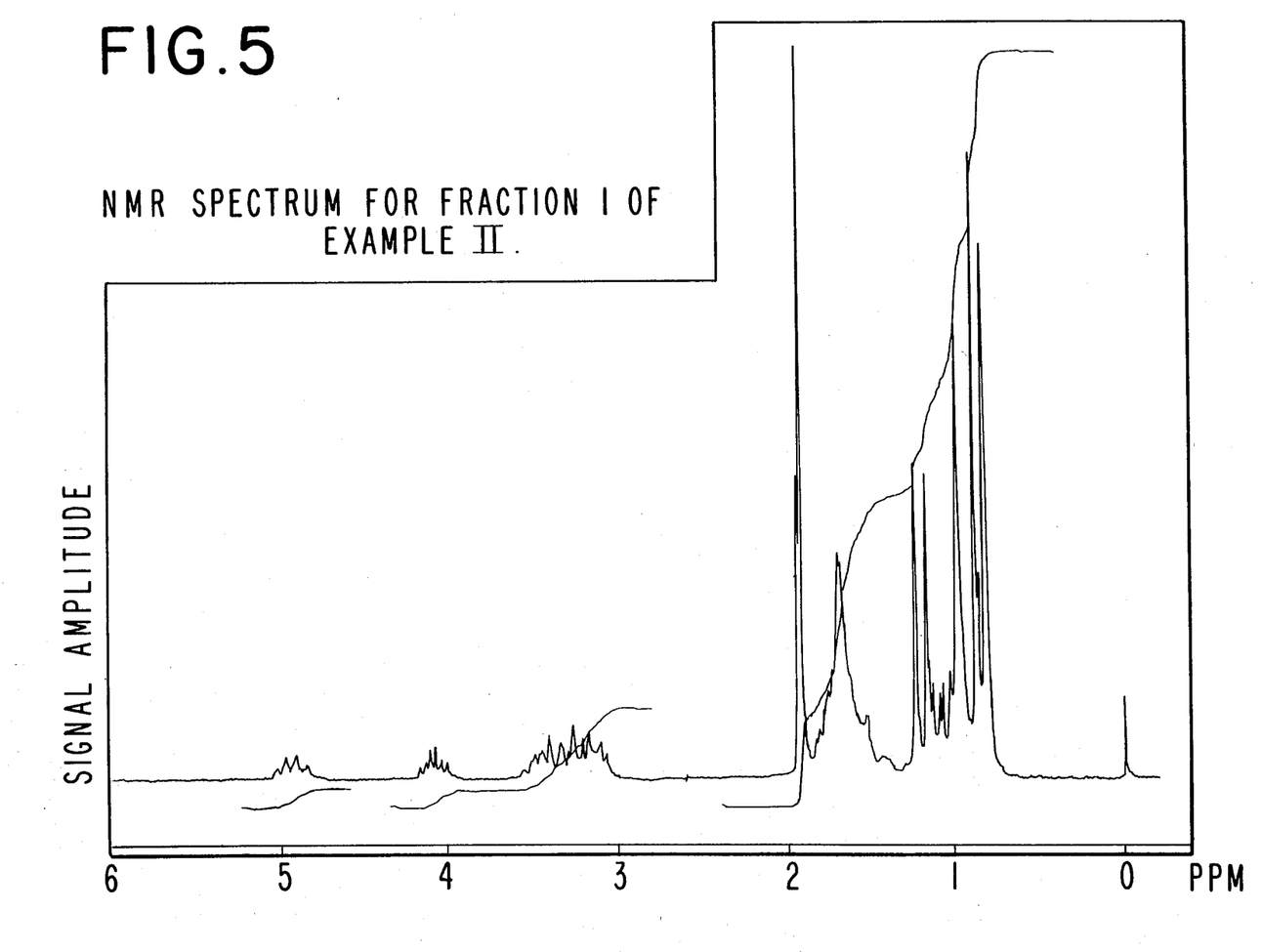
FIG. 5 is the NMR spectrum for fraction 1 of the distillation product of the reaction product of Example II containing the compound having the structure.

FIG. 5 is the NMR spectrum for fraction 1 of the foregoing distillation containing the compound having the structure:

(Conditions: Field strength: 100 MHz; solvent: CFCl$_3$).

EXAMPLE III

Perfume Formulation

The following "woody cologne" perfume formulation is prepared:

| INGREDIENTS | PARTS BY WEIGHT |
|---|---|
| Bergamot oil | 150 |
| Orange oil | 200 |
| Lemon oil | 50 |
| Eugenol | 10 |
| 4-(4-methyl-4-hydroxy amyl) Δ$^3$ cyclohexene carboxaldehyde | 40 |
| Ylang oil | 2 |
| Petitgrain Paraguay | 10 |
| Gamma methyl ionone | 20 |
| Vetiver Venezuela | 18 |
| 3α-Methyl-dodecahydro-6,6,9a-trimethylnaptho-[2,1-b] furan | 5 |
| Product produced by the reaction of acetic anhydride, polyphosphoric acid and 1,5,9-trimethyl cyclododecatriene-1,5,9 according to the process of Example 1 of U.S. Letters Patent 3,718,697, the specification for which is incorporated by reference herein | 5 |
| Octahydro-9,9-dimethyl-1,6-methano-naphthalene-1-(2H—ol produced according to Example III of U.S. Letters Patent 3,996,169, the specification for which is incorporated by reference herein | 50 |
| The compound having the structure:  prepared according to Example II | 12 |

The compound having the structure:

prepared according to Example II imparts a warm, patchouli-like, sandalwood-like, woody aroma to this "woody cologne" composition. Accordingly, the composition can be described as a "woody cologne" composition with warm, patchouli-like, sandalwood-like and woody undertones and patchouli-like, woody and velvety topnotes.

EXAMPLE IV

Preparation of Cosmetic Powder Composition ball mill 100 grams of talcum powder with 0.25 grams of each of the substances set forth in Table I below. Each of the cosmetic powder compositions has an excellent aroma as described in Table I below:

TABLE I

| SUBSTANCE | AROMA DESCRIPTION |
|---|---|
| Compound having the structure:  produced according to Example II | A woody, patchouli, sandalwood-like aroma with woody, patchouli and velvety topnotes. |
| Perfume composition of Example III | A "woody cologne" composition with warm, patchouli-like, sandalwood-like, and woody undertones and patchouli-like, woody and velvety topnotes. |

EXAMPLE V

Perfumed Liquid Detergent

Concentrated liquid detergents with aromas as set forth in Table I of Example IV (which detergents are prepared from Lysine salt of n-dodecyl benzene sulfonic acid as more specifically described in U.S. Pat. No. 3,948,818 issued on Apr. 6, 1976, the specification for which is incorporated by reference herein) are prepared containing each of the substances set forth in Table I of Example IV, supra. They are prepared by adding and homogeneously mixing the appropriate quantity of perfumery substance as set forth in Table I of Example IV in the liquid detergent. The detergents all possess aromas as set forth in Table I of Example IV, the intensity increasing with greater concentrations of perfumery substance of Table I of Example IV, supra.

EXAMPLE VI

Preparation of a Cologne and Handkerchief Perfume

The perfume substances of Table I of Example IV, supra, are incorporated into colognes at concentrations of 1.5%, 2.0%, 2.5%, 3.0% and 4.0% in 80%, 85%, and 90% aqueous ethanol; and into a handkerchief perfume composition at concentrations of 10%, 15%, 20%, 25% and 30% (in 85%, 90% and 95% aqueous ethanol). Distinct and definitive aromas as set forth in Table I of Example IV are imparted to the cologne and to the handkerchief perfume compositions.

EXAMPLE VII

Preparation of a Detergent Composition

A total of 100 grams of a detergent powder (a non-ionic detergent powder containing a proteolytic enzyme prepared according to Example I of Canadian Letters Pat. No. 985,190 issued on Mar. 9, 1976, the disclosure of which is incorporated by reference herein) is mixed with 0.15 grams of each of the substances set forth in Table I of Example IV, supra, until substantially homogeneous compositions are obtained. These compositions have excellent aromas as set forth in Table I of Example IV.

EXAMPLE VIII

Preparation of Soap

Each of the perfumery substances of Table I of Example IV are incorporated into soap (LVU-1) at 0.1% by weight of each substance. After two weeks in the oven at 90° F., each of the soaps showed no visual effect from the heat. Each of the soaps manifested an excellent aroma as set forth in Table I of Example IV, supra.

EXAMPLE IX

Preparation of Soap Composition

One hundred grams of soap chips (IVORY ®, registered trademark of the Procter & Gamble Co. of Cincinnati, Ohio) are mixed individually with one gram each of the perfumery substances of Table I of Example IV, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table I of Example IV, supra.

EXAMPLE X

Preparation of a Solid Detergent Composition

A detergent is prepared from the following ingredients according to Example I of Canadian Letters Pat. No. 1,007,948, the specification for which is incorporated by reference herein:

| Ingredients | Parts by Weight |
|---|---|
| "Neodol 45-11" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table I of Example IV, supra. The detergent samples each have excellent aromas as set forth in Table I of Example IV, supra.

EXAMPLE XI

Utilizing the procedure of Example 1 at column 15 of U.S. Pat. No. 3,632,396 (the specification for which is incorporated by reference herein), a non-woven cloth substrate useful as a dryer-added fabric softening article of manufacture is prepared, wherein the substrate, the substrate coating and the outer coating and the perfuming material are as follows:
1. a water "dissolvable" paper ("Dissolvo Paper")
2. Adogen 448 (m.p. about 140° F.) as the substrate coating; and
3. an outer coating having the following formulation (m.p. about 150° F.);
   57 percent $C_{20-22}$HAPS
   22 percent isopropyl alcohol

20 percent antistatic agent 1 percent of one of the perfume substances of Table I of Example IV, supra.

A fabric softening composition prepared as set forth above having the above aroma characteristics as set forth in Table I of Example IV, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table I of Example IV is imparted in a pleasant manner to the headspace in the dryer on operation thereof, using said dryer-added fabric softening non-woven fabric.

What is claimed is:

1. The 2-acetoxy-4-(2-bornyloxy)butane having the structure:

* * * * *